Figure 1:
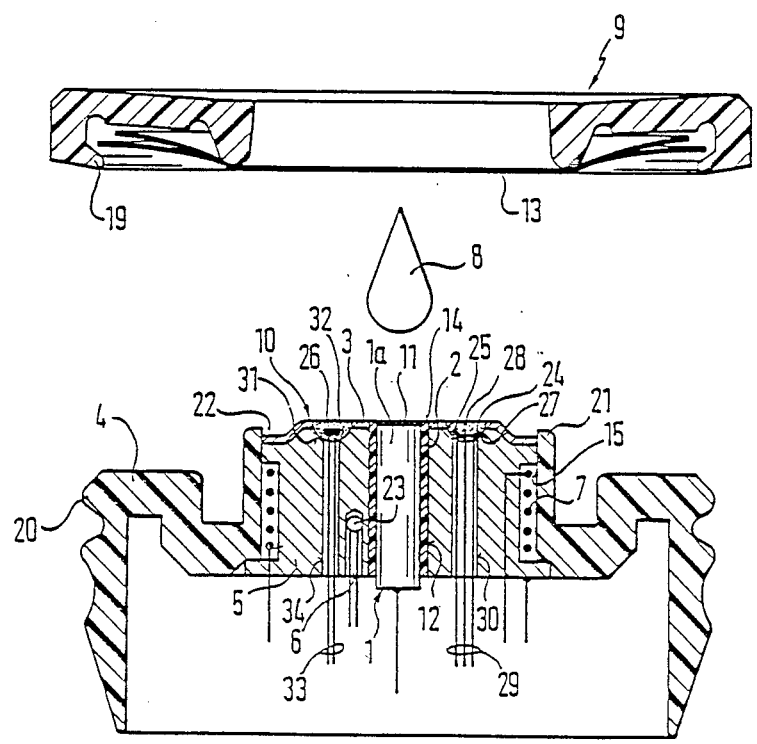

United States Patent [19]

Ullrich

[11] Patent Number: 4,840,179

[45] Date of Patent: Jun. 20, 1989

[54] COMBINED SENSOR FOR THE TRANSCUTANEOUS MEASUREMENT OF OXYGEN AND CARBON DIOXIDE IN THE BLOOD

[75] Inventor: Georg J. Ullrich, Freiburg im Breisgau, Fed. Rep. of Germany

[73] Assignee: Hellige GmbH, Freiburg, Fed. Rep. of Germany

[21] Appl. No.: 121,713

[22] Filed: Nov. 17, 1987

[30] Foreign Application Priority Data

Nov. 17, 1986 [EP] European Pat. Off. ........ 86115941.6

[51] Int. Cl.$^4$ .............................................. A61B 5/00
[52] U.S. Cl. .................... 128/633; 128/635; 128/664; 128/666
[58] Field of Search ................ 128/633, 635, 664–667

[56] References Cited

U.S. PATENT DOCUMENTS

| | | | |
|---|---|---|---|
| 3,628,525 | 12/1971 | Polanyi et al. | 128/633 |
| 3,769,974 | 11/1973 | Smart et al. | 128/666 |
| 4,259,963 | 4/1981 | Hoch | 128/635 |
| 4,621,643 | 11/1986 | New, Jr. et al. | 128/633 |

FOREIGN PATENT DOCUMENTS 3232515 3/1984 Fed. Rep. of Germany ...... 128/635

OTHER PUBLICATIONS

Parker, "Continuous Measurement . . . Saturation", Monitoring . . . Circulation, 1980, pp. 23–28.
Krauss et al., "Noninvasive . . . infants", The J of Pediatrics, vol. 93, No. 2, pp. 275–278, 1978.

*Primary Examiner*—Lee S. Cohen
*Attorney, Agent, or Firm*—Edward J. Whitfield

[57] ABSTRACT

The combined sensor with a thermostatted heating device (7, 23) for the simultaneous and continuous transcutaneous measurement of oxygen ($O_2$) and of carbon dioxide ($CO_2$) in the blood contains a measuring device (1) for the partial pressure of $CO_2$ ($pCO_2$), in which there is pure optical/spectrometric operation or which operates on the principle of pH measurement in an electrolyte (8), and which is separated from the measuring site on the skin by a membrane (13) which is permeable to both $CO_2$ and light, and contains another measuring device (24, 25, 26) for the spectrometric measurement of the blood oxygen saturation ($sO_2$). The advantage over a known $pO_2/pCO_2$ combined sensor is that the combined sensor according to the invention can be operated at a low operating temperature of, for example, 42° C. or less, so that continuous measurement for 24 hours, for example, is possible without resiting or recalibrating the sensor, and thus it is simple to use in the domestic milieu.

5 Claims, 2 Drawing Sheets

COMBINED SENSOR FOR THE TRANSCUTANEOUS MEASUREMENT OF OXYGEN AND CARBON DIOXIDE IN THE BLOOD

The invention relates to a combined sensor for the transcutaneous measurement of oxygen ($O_2$) and carbon dioxide ($CO_2$) in the blood.

Measuring sensors for the transcutaneous monitoring of the blood gases $O_2$ and/or $CO_2$ have been disclosed. It has also been disclosed, in DE-C3-21 45 400, for such measuring sensors, which are also called measuring probes or, for brevity, sensors, to heat electrically a metal body which acts as a reference or counter electrode, and to maintain at a constant temperature via a control device. The electrical heating has two functions in this. On the one hand, the warming generates hyperaemia of the skin and tissue underneath the measuring probe and, on the other hand, maintenance of a constant temperature of the measuring probe stabilizes the properties of the physical or electrochemical measuring elements contained therein. In addition, under certain conditions, the heat input required to maintain the temperature of the measuring probe can be used to monitor the relative local blood flow; compare the book by Huch, Huch and Lübbers: Transcutaneous $pO_2$; Thieme Verlag Stuttgart-New York 1981. In the same book, on pages 101 to 107, sensors and measuring devices for the transcutaneous monitoring of the partial pressure of oxygen, $pO_2$, are described, in which the oxygen is measured by polarography, and on pages 78 to 80 it is pointed out that an adequate sensor temperature is necessary for validity of the transcutaneous $pO_2$ monitoring. The minimum temperature for this purpose is regarded as being 43° C.; temperatures up to 45° C are normally used.

In order to avoid skin damage at these temperatures, it is necessary from time to time to place the measuring sensor elsewhere on the surface of the skin; about every 4 hours at an operating temperature of 43° C. This circumstance demands attention and supervision by reliable personnel, which, experience has shown, cannot be assumed in the domestic milieu. A procedure which is practised in order to be able, nevertheless, to carry out such monitoring entails use of two sensors which are alternatively heated for a certain time and used for $pO_2$ measurement; compare the article by PETER, H.J.; Holter Monitoring Technique in a Comprehensive Approach: Ambulatory Monitoring of Sleep Apnea; in Holter Monitoring Technique, Hergb.: HOMBACH-/HILGER; VERLAG SCHATTAUER Stuttgart-New York 1985, page 134/135. However, the disadvantages of this solution are that two sensors are required, which leads to difficulties, especially with small children, and that there is a need for complicated electronic means to switch over between the measuring probes at the preset time intervals. In addition, problems derive from the identical calibration of the two sensors, which is necessary.

Measuring probes for the transcutaneous monitoring of carbon dioxide ($CO_2$) are described in, for example, DE-A1-29 11 343 and DE-A1-32 32 515. These measuring sensors contain pH measuring electrodes which measure the pH in a thin layer of an electrolyte solution which is enveloped by a $CO_2$-permeable membrane and is subject to gas exchange, via diffusion of $CO_2$ gas, with the material which is to be measured. In this, the pH is measured either with a known glass electrode, as has been known for a long time in blood gas analysers, for example in the embodiment in DE-A1 21 11 343, or more recently, with a special iridium/iridium oxide electrode, as described in DE-A1-32 32 515.

It is desirable, and in critical cases necessary, to monitor both the oxygen and the carbon dioxide. Accordingly, DE-A1-23 05 049 discloses the proposal, which is obvious per se, to combine the sensors for $pO_2$ and $pCO_2$ spatially in one sensor housing. This proposal has now led to combined $pO_2/pCO_2$ sensors which must likewise be heated to at least 43° C. to ensure satisfactory $pO_2$ measurement. In addition recalibration at defined time intervals is necessary for the part measuring $pCO_2$, which is effected, for example as specified in DE-A1-23 05 049, by a glass electrode.

The invention is based on the problem of providing a combined sensor or combined measuring probe for the simultaneous and continuous transcutaneous measurment of carbon dioxide and oxygen in the blood for a prolonged period, for example throughout a day or a night, using a single sensor for monitoring, without it being necessary to interrupt this monitoring to resite the sensor, to switch over to another sensor, or for calibration procedures.

There is a need for a solution to this problem in, for example, the monitoring of patients with nocturnal breathing disorders or of children threatened by the socalled sudden infant death syndrome (=SIDS). This is because it has emerged that, where possible, such patients should also be monitored in their natural surroundings in the domestic milieu, whether for more accurate diagnosis of their disorder or in a period of transition from clinical supervision to the domestic milieu in which there appears to be an indication, for safety reasons, for the monitoring which was carried out in the hospital to be continued at home to a cetain minimal extent. However, it must be possible even for non-experts to operate a measuring device for monitoring of this type in the domestic milieu without fear of unreliable measurement or risk to the patient.

The solution according to the invention, as stated in patent claim 1, is based on the idea of making the possibility of uninterrupted transcutaneous $pCO_2$ monitoring for a prolonged period utilizable for a combined, transcutaneously measuring, oxygen/carbon dioxide sensor in such a way, which differs from solutions hitherto disclosed, that in one measuring sensor a $pCO_2$ measuring device is combined not with one for measuring the partial pressure of oxygen, $pO_2$, but with a measuring device for the spectrophotometric measurement of the oxygen saturation of the blood, $sO_2$. In the first place, this eliminates the problem of local overheating of the measuring site on the skin, since heating of the skin to 43° C. or more is no longer necessary.

It was possible to solve the other problem of the calibration at intervals of the part of the sensor for $pCO_2$ monitoring, which was hitherto necessary, by the surprising finding that measuring sensors for transcutaneous $pCO_2$ measurement, as are described in DE-A1-32 32 515 and which are thus equipped with an iridium-/iridium oxide electrode for pH measurement, have such low drift that they can be operated at a lower operating temperature of, for example, 42° C. without calibration at intervals, i.e. without interruption of monitoring, for 24 hours, and can be left on a site on the patient's skin without skin damage.

It has also emerged that, in many cases, measurement of the blood oxygen saturation, $sO_2$, is sufficient for monitoring patients. This particularly applies to the use in the domestic milieu which has been described, for example, for monitoring children at risk of SIDS or patients at risk of nocturnal apnoea.

According to a first variant of the teaching of the invention, a combined sensor for the transcutaneous measurement of oxygen ($O_2$) and carbon dioxide ($CO_2$) in the blood contains a measuring device for $pCO_2$ based on the principle of pH measurement in an indicator solution, and a measuring device for the spectrophotometric determination of the oxygen saturation $sO_2$, which may consist of a combination of light-emitting diodes, which emit light of various wavelengths, and of one or more photoelectric receivers pertaining thereto. The input and output of light can also take place via light guides, with the spectral light generation and measurement taking place in the evaluation apparatus. The wavelengths of two light-emitting diodes in the preferred embodiment of the invention are chosen to be, in one case, in the infrared region, in particular isosbestic for haemoglobin or oxyhaemoglobin and preferably at $\lambda=805$ nm, with the other wavelength in the red region, in particular at about $\lambda=650$ nm.

It is particularly expedient for the signal evaluation to be based on the principle of pulse oximetry, i.e. to undertake the light-emitting diodes and/or the signal evaluation intermittently and harmonized to the pulse phases of the arterial filling of the area measured. This principle is known per se and described, for example, in an article by Yoshia/Shimada/Tanaka: Spectrophotometric Monitoring of Arterial Oxygen Saturation in the Fingertip, Med. Biol. Engng. Comput. 18:27–32 (1980). An earlier fundamental description of the procedure of oximetry and its historical development is to be found, for example, in ULLRICH: Physikalischtechnisches zur Oxymetrie und Farbstoffinjektionsmethode (Physical and technical aspects of oximetry and the dye injection method); HELLIGE Mitteilungen für die Medizin, No. 7, pages 4 to 16 (1964).

Thus, the invention has produced a combined measuring probe or sensor for the simultaneous, continuous transcutaneous measurement of the partial pressure of carbon dioxide in the blood ($tcpCO_2$) and of the oxygen saturation ($tcsO_2$) in the blood, which can be stuck onto the skin like known small sensors, and needs to be heated to and thermostated at a temperature of only 42° C. or less, the additional advantage which is achieved at these operating temperatures being that the quality of the pulseoximetric measurement signal is distinctly improved and stabilized.

In the second basis embodiment of the invention there is pure optical/spectrophotometric measurement both of the partial pressure of carbon dioxide, $pCO_2$ and of the oxygen saturation, $sO_2$. In this case, a pH colour indicator is used and is present in a thin layer which is bonded with, for example, acrylic resin and is in contact with the electrolyte.

The invention and advantageous details are explained in detail hereinafter on the basis of an exemplary embodiment and with reference to the drawing.

Figure 2:
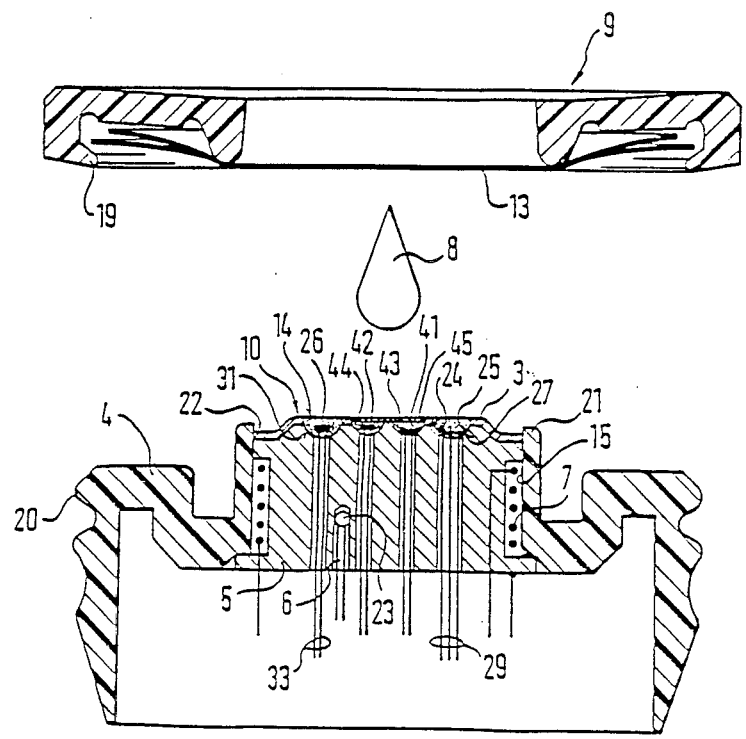

FIG. 1 shows a diagrammatic representation of a section through a combined sensor according to the invention, based on the first variant of the inventive concept, and FIG. 2 shows an exemplary embodiment corresponding to the representation in FIG. 1 for a combined sensor based on the second solution principal.

The drawing of FIG. 1 shows an annular housing 4 which is composed of plastic and has a central orifice 15 into which is inserted an exactly fitting metal body 5 which is preferably composed of silver (Ag) and, in the representation, is provided on the upper side, i.e. the (subsequent) measuring surface 10, with a covering silver/ silver chloride reference electrode 3. The orifice 15 is delimited by a cylindrical wall 21 which projects all round slightly beyond the surface of the reference electrode 3 so that, in addition, due to a setting back of the reference electrode 3 at the edge, there is formation of an electrolyte reservoir 22. The metal body 5 has a central perforation 12 which also passes through the reference electrode 3 and into which is fitted in concentric arrangement a pH-measuring electrode 1 which, in the preferred embodiment, is an iridium/iridium oxide (Ir/IrOx) electrode and which, for example, has a diameter of 2 mm. This electrode 1 is insulated against the reference electrode 3 and against the metal body 5 by a cast synthetic resin layer 2. As is disclosed in DE-A1-32 32 515, the Ir/IrOx electrode 1 can be produced from a single cylindrical piece of iridium which is oxidized on the surface side, that is to say on the surface which faces a membrane 13 and is immersed in an electrolyte 8. However, iridium is comparatively a very costly metal. For this reason, merely on the grounds of cost, it will as a rule be advantageous to provide the body of the Ir-/IrOx electrode 1 on the face, i.e. on the surface which is immersed in the electrolyte 8 with an iridium disc 11 which has a connection of good electrical and thermal conductivity to the remainder of the electrode body 1a, which can be composed of, for example, silver or copper. The surface of the iridium disc 11 which is immersed in the electrolyte 8 is in this case oxidized electrochemically or thermochemically, it also being possible for the oxide to be present in hydrated form as iridium oxide hydrate. The reference electrode 3 is either formed by an at least partially chlorinated surface of the metal body 5 which is composed of silver, or plated onto the metal body 5 as an annular disc of silver/silver chloride sintered metal. The metal body 5 is provided in the region of its enveloping surface shell with a wide, encircling annular channel into which a heating coil 7 is inserted. The heat input supplied to the metal body 5 is controlled by at least one temperature probe, for example a thermistor 23, inserted in an excentric perforation 6. Another temperature probe (which is not shown), which is again a thermistor for example, can be inserted in a manner known per se into the metal body 5, and controls a switch unit (which is not shown) for direct interruption of the heat input supplied to the heating coil 7 when the temperature in the metal body exceeds a threshold figure, which can be preset, of 42° C. for example.

The $pCO_2$ measuring device with a pH measuring electrode, which has been described thus far and is known per se, for example from DE-A1-32 32 515, is combined according to the invention with an $sO_2$ measuring device which, in the first embodiment which is presented, is composed, on the one hand, of two photoelectric emitter units in the form of two light-emitting diodes 24 and 25 and, on the other hand, of a photoelectric receiver unit 26 which will preferably be a silicon photoelement (Si photoelement). The two light-emitting diode units 24 and 25 are inserted in a bowl-like recess 27 in the layer of Ag/AgCl of the reference electrode 3 and of the metal body 5, which recess is filled in a moisture- and airtight manner with a light-transmitting casting composition 28 which is ground flat and polished on the surface side, i.e. on the measuring surface side facing the membrane 13. The light-transmitting casting composition 28 can also act as an (additional) passivating layer for the light-emitting diodes 24 and 25. The sides of the diodes 24 and 25 from which the light emerges are pointed towards the layer of the electrolyte 8, which is present between the measuring surface and the membrane after the completion of the sensor which is described hereinafter, in such a way that their beams do not mutually interfere. The signal is supplied to the diodes 24 and 25 via lead wires 29 which pass through a perforation 30 in the metal body 5. The perforation 30 can likewise be filled with a suitable casting resin.

The photoelectric receiver unit 26 is inserted in a manner similar to the diodes 24 and 25 into a bowl-like recess 31 using a casting composition 32, which likewise transmits light, and is aligned with the measuring surface or the membrane 13 and the (subsequent) electrolyte layer 8. The signal is taken off via lead wires 33 which pass through another perforation 34, which is likewise filled with set casting resin in the final state of the sensor, in the metal body 5.

On appropriate excitation, the two light-emitting diodes 24 and 25 emit light of different wavelengths. One of these wavelengths is chosen to accord with the extinction coefficients of haemoglobin and oxyhaemoglobin, or in other words isosbestic for haemoglobin and oxyhaemoglobin, in the infrared region and, in particular, at $\lambda = 805$ nm, whereas the wavelength for the other diode is chosen in the red region, for example at about $\lambda = 650$ nm. As already mentioned above, the two light-emitting diodes 24 and 25 are triggered, and the signal is evaluated, expediently by the principle of pulse oximetry.

In order to prepare the sensor for a measuring procedure, a small drop of electrolyte 8 is, as is evident from the drawing, placed on the continuous surface 14 (measuring surface) of the reference electrode 3, of the light-transmitting casting compositions 28 and 32 which are polished on the surface side, and of the Ir/IrOx electrode 1. A snap-on ring/membrane device 9 which is preproduced for single use is then clipped onto the combined sensor. The snap-on ring 9 which is manufactured with a slight dishing has an encircling locking edge 19 which projects inwards. When the snap-on ring 9 is pushed onto the housing 4 the locking edge 19 locks behind a projecting rim 20 on the housing, and the membrane 13, which is permeable to $CO_2$ and light, is tensioned over the surface 14, accurately centered, with a thin layer of the electrolyte 8 being interposed. The snap-on ring 9 which holds the membrane 13 precentered and tensioned is known and is described in, for example, DE-A1-30 40 544.

The combined sensor according to the second variant of the invention, in which there is pure optical/ spectrophotometric operation and which is shown in Fig. 2, can, in principle and in terms of the design and external dimensions, be constructed in a similar or identical manner as the combined sensor shown in FIG. 1. The same reference numers are used to identify the corresponding parts and elements which have already been illustrated in FIG. 1.

However, as a modification of the embodiment shown in FIG. 1, the pH-measuring electrode 1 is replaced, for measurement of the partial pressure of carbon dioxide $pCO_2$, by an optical/spectrophotometric measuring device which is essentially composed of a light-emitting diode unit 41, a photoelectric receiving unit 42 and a thin layer of colour indicator which covers this emitter/ receiver combination. Colour indicators suitable for use for spectrophotometric measurement in this case are known to those skilled in the art. In an advantageous embodiment the colour indicator is, for example, bound in a thin layer of acrylic resin which is embedded in the form of a disc as an intermediate layer 45 in the measuring surface 14. If the pH of the electrolyte 8 changes there is an alteration in the light absorption or light reflection properties of the colour indicator bound in the acrylic resin disc 45. In the case of FIG. 2 too, the light-emitting diode unit 41 and the photoelectric receiver unit 42 are inserted into depressions in the measuring surface 14 which are filled with casting resin 43 and 44, respectively.

In the embodiments shown in FIG. 1 as well as that shown in FIG. 2 it is possible for the light-emitting diodes 24, 25, 41 and the photoelectrical receiver units 26, 42 to be located elsewhere, for example in the measuring apparatus itself, and the light can be guided towards and away from the measuring surface 14 by thin glass fibres.

I claim:

1. A sensor element for simultaneous, continuous, transcutaneous measurement of the partial pressure of carbon dioxide and of the oxygen saturation in the blood of a living body, said sensor element comprising:
   a housing having a planar measuring surface;
   a membrane, permeable to carbon dioxide, sealably disposed about the measuring surface, said membrane having inner and outer surfaces;
   a reference electrode and a measuring electrode embedded in the measuring surface and electrically insulated each from the other;
   two light emitting diodes embedded in the measuring surface each emitting light of different wave length and so positioned that the emitted light beams do not mutually interfere;
   photoelectric receptor means embedded in the measuring surface; and
   a thin layer of electrolyte disposed between the measuring surface and the inner surface of the membrane;
   whereby when the outer surface of the membrane is brought in contact with the skin, carbon dioxide diffuses through the membrane changing the pH of the electrolyte solution which change in pH is sensed by the reference electrode and the measuring electrode which change in pH is related to the partial pressure of carbon dioxide and whereby the light emitted from the diodes after diffusion through the skin is detected by the photoelectric receptor means and the oxygen saturation of the blood is determined by the principle of pulse oximetry.

2. The sensor element of claim 1 wherein said housing has a heating coil embedded therein.

3. The sensor element of claim 1 wherein the reference electrode is a silver/silver chloride electrode and the measuring electrode is an iridium/iridium oxide electrode.

4. The sensor element of claim 1 wherein one of the diodes emits light at a wavelength in the infrared region of the electromagnetic spectrum and the other diode emits light at a wavelength in the red region of the electromagnetic spectrum.

5. The sensor element of claim 4 wherein the infrared wavelength is 805 nanometers and the red wavelength is 650 nanometers.

* * * * *